United States Patent [19]

Hughes et al.

[11] Patent Number: 4,976,837

[45] Date of Patent: Dec. 11, 1990

[54] BLOCKED ISOCYANATES

[75] Inventors: Anthony H. Hughes, Rossendale; Arthur Topham, Middleton, both of United Kingdom

[73] Assignee: The Baxenden Chemical Co., Lancashire, England

[21] Appl. No.: 892,898

[22] Filed: Aug. 1, 1986

Related U.S. Application Data

[62] Division of Ser. No. 706,391, Feb. 27, 1985, abandoned.

[30] Foreign Application Priority Data

Feb. 29, 1984 [GB] United Kingdom ............... 8405320

[51] Int. Cl.$^5$ ............................................. C25D 13/06
[52] U.S. Cl. .............................. 204/181.7; 106/287.2
[58] Field of Search .................. 204/181.7; 106/287.2

[56] References Cited

U.S. PATENT DOCUMENTS

| | | | |
|---|---|---|---|
| 3,721,645 | 3/1973 | Zemlin | 260/45.8 N |
| 4,008,247 | 2/1977 | Tucker | 548/261 |
| 4,246,087 | 1/1981 | Tsou | 204/181.7 |
| 4,285,789 | 8/1981 | Kobayashi | 204/181.7 |
| 4,293,398 | 10/1981 | Prucnal | 204/181.7 |
| 4,335,228 | 6/1982 | Beitchmann et al. | 525/528 |

FOREIGN PATENT DOCUMENTS

| | | | |
|---|---|---|---|
| 414259 | 7/1974 | U.S.S.R. | |
| 1592516 | 7/1981 | United Kingdom | 548/374 |

OTHER PUBLICATIONS

Weber, Chem Abst. 83, 186262d (1975).

*Primary Examiner*—John F. Niebling
*Assistant Examiner*—Isabelle Rodriguez
*Attorney, Agent, or Firm*—Nixon & Vanderhye

[57] ABSTRACT

A blocked polyisocyanate of the formula $$R-Y_m$$

where R is an m valent aliphatic, cycloaliphatic, heterocyclic or aromatic residue;
each Y, which may be the same or different, is

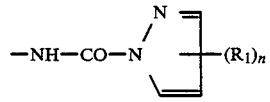

where $R_1$ is, or, when n is more than 1, each $R_1$, which may be the same or different, is an alkyl, alkenyl, aralkyl, N-substituted carbamyl, phenyl, $NO_2$, halogen or

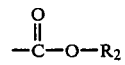

group where $R_2$ is a $C_1$–$C_4$ alkyl group;
n is 0, 1, 2 or 3; and
m is an integer greater than 1 is useful in paint compositions.

16 Claims, No Drawings

BLOCKED ISOCYANATES

This is a division of application Ser. No. 706,391, filed Feb. 27, 1986, now abandoned.

The present invention relates to novel blocked polyisocyanates, methods for making them, coating and other compositions e.g. paints and elastomers, containing them and methods of electrodeposition of the coating compositions.

Blocked polyisocyanates are commonly used in paints which also contain active hydrogen containing compounds e.g. amines and alcohols. Certain of these paints can be electrophoretically or conventionally e.g. spray deposited onto the article to be coated and then subsequently hardened by heating, often referred to as stoving. During stoving the blocked polyisocyanates dissociate so that the isocyanate groups become available to react with the active hydrogen containing compounds leading to crosslinking and hardening of the paint.

Blocked polyisocyanates reacting with any active hydrogen containing compound for the purposes of curing by chain extension or crosslinking are also used in cross-linking acrylic resins for automotive priming and finishing, formulating one-pack elastomers and surface coatings which contain the blocked isocyanate and as a chain extender in a single storage stable package which, when cast, can be cured by application of temperatures above the unblocking temperature.

Blocked polyisocyanates are polyisocyanates in which each isocyanate group has reacted with a protecting or blocking agent to form a derivative which will dissociate on heating to remove the protecting or blocking agent and release the reactive isocyanate group.

Compounds already known and used as blocking agents for polyisocyanates include aliphatic, cycloaliphatic or aralkyl monohydric alcohols, hydroxylamines and ketoximes.

Currently used blocked polyisocyanates dissociate at temperatures of around 160° C. If a blocked polyisocyanate could be used which dissociated at a lower temperature but was still stable at ambient temperatures, then heat sensitive materials could be utilised and energy savings could be made. The blocked polyisocyanates of the present invention dissociate at a significantly lower temperature than those currently used and are easily made. The presence of a catalyst is preferred in order to increase the rate of reaction between the liberated polyisocyanate and the active hydrogen containing compound, especially if the active hydrogen group is —OH. The catalyst can be any catalyst known in the art, e.g. dibutyl tin dilaurate or triethylene diamine.

The present invention comprises a compound of the formula:

$$R\text{-}Y_m \quad (I)$$

where R is an m valent aliphatic, cycloaliphatic, heterocyclic or aromatic residue and each Y, which may be the same or different, is

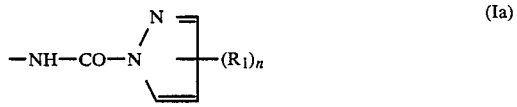

where $R_1$ is, or, when n is more than 1, each $R_1$, which may the same or different, is an alkyl, alkenyl, aralkyl, N-substituted carbamyl, phenyl, $NO_2$, halogen or

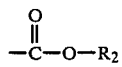

group where $R_2$ is a $C_1$-$C_4$ alkyl group,
n is 0, 1, 2 or 3
and m is an integer >1, preferably 2-6.

When $R_1$ represents an alkyl or alkenyl group it preferably contains up to 4 carbon atoms. When it is an aralkyl group, it is preferred that the aryl portion is phenyl and that the alkyl portion contains 1 to 4 carbon atoms. When $R_1$ is a halogen, it is preferably chlorine or bromine.

The blocking agents used in the present invention are pyrazoles of the formula:

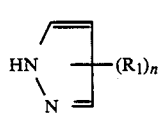

where $R_1$ and n are as defined above. Examples of the pyrazoles described include 3,5-dimethylpyrazole, 3-methylpyrazole, 4-nitro-3,5-dimethylpyrazole and 4-bromo-3,5-dimethylpyrazole.

The preferred blocking agent is 3,5-dimethylpyrazole.

Some of these pyrazoles can be made by converting acetylacetone (AA) into a derivative which will react with hydrazine to give the desired pyrazole e.g.

$$AA + Na + CH_2\!=\!CHCH_2Cl \rightarrow Ac_2CHCH_2CH\!=\!CH_2$$

$$AA + Na + PhCH_2Cl \rightarrow Ac_2CHCH_2Ph$$

$$AA + PhNCO \rightarrow Ac_2CHCONHPh$$

The polyisocyanate which is to be blocked may be any organic polyisocyanate suitable for crosslinking compounds containing active hydrogen e.g. aliphatic including cycloaliphatic, aromatic, heterocyclic, and mixed aliphatic aromatic polyisocyanates containing 2, 3 or more isocyanate groups. The group R will normally be a hydrocarbon group but substitution e.g. by alkoxy groups is possible.

The isocyanate compound may be, for example, ethylene diisocyanate, propylene diisocyanate, tetramethylene diisocyanate, hexamethylene diisocyanate, decamethylene diisocyanate, dodecamethylene diisocyanate, 2,4,4-trimethylhexamethylene-1,6 diisocyanate, phenylene diisocyanate, tolylene or naphthylene diisocyanate, 4,4'-methylene-bis(phenyl isocyanate), 4,4'-ethylene-bis (phenyl isocyanate), ω,ω'-diisocyanato-1,3-dimethyl benzene, ω,ω'-diisocyanato-1,4-dimethyl cyclohexane, ω, ω'-diisocyanato-1,4-dimethyl benzene, ω, ω'-diisocyanato-1,3-dimethylcyclohexane, 1-methyl- 2,4-diisocyanato cyclohexane, 4,4'-methylene-bis (cyclohexyl isocyanate), 3-isocyanato-methyl-3,5,5-trimethyl cyclohexyl isocyanate, dimer acid-diisocyanate, ω,ω'diisocyanatodiethyl benzene, ω,ω'-diisocyanatodimethyl toluene, ω,ω'-diisocyanato-diethyl toluene, fumaric acid-bis (2-isocyanato ethyl) ester or triphenyl-methane-triisocyanate, 1,4-bis-(2-isocyanato-prop-2yl) benzene, 1,3-bis-(2-isocyanato prop-2yl) benzene, but is preferably free from isocyanate groups directly attached to aromatic nuclei.

Use can also be made of polyisocyanates obtained by reaction of an excess amount of the isocyanate with (a) water, (b) a lower molecular weight polyol (e.g. m.w.≦300) or (c) a medium molecular weight polyol, e.g. a polyol of greater than 300 and less than 8000 m.w., eg sucrose, or by the reaction of the isocyanate with itself to give an isocyanurate.

The lower molecular weight polyol comprises, for example, ethyleneglycol, propyleneglycol, 1,3-butylene glycol, neopentyl glycol, 2,2,4-trimethyl-1,3-pentane diol, hexamethylene glycol, cyclohexane dimethanol, hydrogenated bisphenol-A, trimethylol propane, trimethylol ethane, 1,2,6-hexane triol, glycerine, sorbitol or pentaerythritol.

The di- or poly-isocyanate obtained by the above reaction may have a biuret structure, or an allophanate group.

The blocked polyisocyanate of the formula I is formed by admixing the polyisocyanate

 $R(NCO)_m$ (III)

with a sufficient quantity of a pyrazole of the formula:

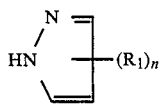 (II)

such that the reaction product contains no free isocyanate groups and is a urea of formula I. This reaction is exothermic and since the reaction product will dissociate if the temperature is raised sufficiently, cooling may be required to keep the temperature of the reaction mixture down, preferably to 80° C. or less.

One use of blocked polyisocyanates is in electrophoretically deposited paints. The invention also comprises a paint composition comprising a pigment carrier containing active hydrogen groups, a pigment and a compound of the formula I.

These paints are usually composed of a pigment dispersed in an aqueous dispersion of a resin containing active hydrogen which is to be crosslinked by the polyisocyanate. Preferably the paint contains 0.5 to 2 blocked isocyanate groups per active hydrogen containing group. Suitable active hydrogen containing resins include polyamide-polyamine resins, e.g. the product from a dimer fatty acid and an aliphatic polyamine, carboxylic acid group containing acrylic resins, and tertiary amine group containing hydroxyacrylic resins and polymers thereof.

The total concentration of the dispersed solids will, of course, depend upon the process for which the paint is to be used. Various standard additives such as surface active agents, catalysts and anti-oxidants may also be incorporated.

The invention also comprises a method of electrodepositing onto substrates a paint composition as described above and then heating the deposited paint to cross link the pigment carrier.

The electrophoretic deposition process is well known and involves the use of a cathode and an anode in contact with a bath containing the paint. The surface to be coated is one of the electrodes. On applying a voltage, generally 1 to 3,000 volts, across the electrodes the paint is deposited over the chosen electrode.

The coated article is removed from the bath and stoved e.g. baked in an oven, in order to release the isocyanate groups which then react with the active hydrogen in the resin to crosslink and harden the coating. Using coating compositions according to this invention the temperature to which the coated article must be heated is generally 100° to 140° C., which is significantly lower than the temperatures required in current commercial processes of 160° C. or more.

An added advantage of the process of our invention is the ability to block polyisocyanates in the presence of alcoholic solvents, because pyrazoles are much more reactive than alcohols towards polyisocyanates. This also makes it possible to block polyisocyanates at temperatures lower than those used with compounds already known and used as blocking agents for polyisocyanates.

The following Examples illustrate the invention. All parts and percentages are by weight unless otherwise specified.

EXAMPLE 1

A mixture of 292.4 parts of Trixene L75 (which is a polyfunctional isocyanate made by the addition of toluene di-isocyanate and a mixture of trimethylolpropane and diethylene glycol, as a 75% solution in ethyl acetate) and 105.8 parts of ethyl acetate is stirred while 94.9 parts of 3,5-dimethylpyrazole is added during 5 minutes, the temperature rising from 23° C. to 55° C. After 2¾ hours the temperature falls to 27° C. The I.R. Spectrum shows NCO absent.

EXAMPLE 2

A mixture of 91.5 parts of trimethylolpropane, 273.2 parts of propylene carbonate and 454.9 parts of isophorone diisocyanate is stirred for 2½ hours at 70° C. and then held at 55° C. for 16 hours. The product thus formed contains 10.37% NCO. 809.3 parts of this product is stirred at 33° C. while 201.0 parts of 3,5-dimethylpyrazole is added, followed by 470.8 parts of the monomethyl ether of propylene glycol (Dowanol PM). The temperature rises to 52° C. and a clear solution is formed. The IR spectrum shows NCO absent. Analysis shows only 0.5% of free dimethylpyrazole to be present.

EXAMPLE 3

A mixture of 861 parts of isophorone diisocyanate, 535.95 parts of propylene carbonate and 2.15 parts of Dabco TMR* is stirred and gradually heated. When the temperature reaches 55° C. heating is discontinued. The exothermic reaction raises the temperature to 131° C. in 15 minutes. After cooling to 89° C., 5.8 parts of a 10% solution of Dabco TMR* in propylene carbonate is added. The temperature rises to 90° C. in 8 minutes. After heating to 132° C. it is allowed to cool. 1397.1 parts of this product, the tri-isocyanatoisocyanurate formed from 3 moles of isophorone diisocyanate as a 61.4% solids solution in propylene carbonate, having an NCO content of 10.94% is stirred while 366.8 parts of 3,5-dimethylpyrazole is added, cooling as required, to keep the temperature below 80° C. followed by 463.4 parts of the monomethyl ether of propylene glycol. The mixture is stirred at 50° C. and a clear solution formed which solution is then allowed to cool. The IR Spectrum shows NCO absent.

* (Reg. Trade Mark) which is N-Hydroxyalkyl Quaternary Ammonium Carboxylate.

EXAMPLE 4

800 parts of pre-polymer from polypropylene glycol of average molecular weight 1000 and 80:20 2,4:2,6-toluene diisocyanate, containing 5.32% NCO and which has been substantially freed from free toluene diisocyanate by thin film evaporation, is stirred while 102.14 parts of 3,5-dimethylpyrazole is added. After stirring for 1¼ hours the temperature rises from 25° to 46°. The temperature is held at 46° for a further 1¼ hours then raised to 80° during 40 minutes and held at 80° for 110 minutes. The product is a clear pale amber-coloured liquid.

EXAMPLE 5

The preparation referred to in Example 2 above using 3,5-dimethylpyrazole (3,5-DMP) as the blocking agent, was repeated but methyl ethyl ketoxime (MEKO) was used as the blocking agent. The products of each of these preparations was then mixed with the stoichiometric quantity of 1,4-butanediol and 1% dibutyl tin dilaurate was added and then the mixture was coated onto steel panels. The coatings were allowed to dry at room temperature for 5 days and then stoved in an oven at the specified temperature for 30 minutes. The panels were then tested for pencil hardness as an indication of cure.

| Temperature in °C. | MEKO Blocked | 3,5-DMP Blocked |
|---|---|---|
| 100 | Fails HB, no cohesive strength | Fails HB, no cohesive strength |
| 120 | Fails HB, no cohesive strength | Passes 5H, cohesive film |
| 135 | Fails HB, no cohesive strength | Passes 7H, cohesive film |
| 160 | Passes 7H, cohesive film | Passes 7H, cohesive film |

The above results show an almost 40° C. improvement in cure temperature with the 3,5-dimethylpyrazole blocked polyisocyanate.

EXAMPLE 6

A paint base is made from the following:

| | | parts |
|---|---|---|
| 1. | Xylene | 7.90 |
| 2. | Titanium Dioxide RTC60 *(1) | 38.27 |
| 3. | Additive T.I. *(2) | 1.60 |
| 4. | 10% Acronal 700L Solution in Xylene *(3) | 0.40 |
| 5. | Multiflow *(4) | 0.13 |
| 6 | Synocure 867S *(5) | 51.70 |

METHOD

Charge the Xylene, Additive T.I., 10% Acronal Solution and Multiflow, gradually adding the Titanium Dioxide and half of the Synocure to give sufficient wetting for efficient grinding. Grind under high shear to Hegmann 5, then add the rest of the Synocure.

| *(1) RTC60 | Tioxide U.K. Ltd. |
|---|---|
| *(2) Additive T.I. | Bayer U.K. Ltd. |
| *(3) Acronal 700L | BASF U.K. Ltd. |
| *(4) Multiflow | Monsanto PLC |
| *(5) Synocure 867S | Cray Valley Products Ltd. |

A mixture of 58.0 parts of the above described paint base, 22.2 parts of the product from Example 2 and 0.4 part of dibutyltin dilaurate was coated on two steel panels and allowed to dry for seven days at ambient temperature. One panel was stoved for ½ hour at 120°, and the other for ¾ hour at 100° C. Tests for pencil hardness showed that both passed 5H.

Similar results (5H) pencil hardness) were obtained using equivalent amounts of the products prepared as described in Example 2 but using instead of 3,5-dimethylpyrazole the equivalent amounts of 4-nitro-3,5-dimethylpyrazole, 4-benzyl-3,5-dimethylpyrazole, methyl 5-methylpyrazole-3-carboxylate, 4-bromo-3,5-dimethylpyrazole, pyrazole, 3-methyl-5-phenylpyrazole and 3,5-dimethylpyrazole-4-carboxanilide (prepared by condensation of hydrazine acetate with diacetoacetanilide). A similar result was also obtained using a product prepared as described in Example 2 but using Pentoxone* (4-methoxy-4-methylpentan-2-one) instead of propylene carbonate. A panel coated with the paint base and stoved for 1 hour at 120° with no cross-linker present failed an HB pencil test.

*Pentoxone—Shell Chemicals PLC

We claim:

1. In a storage-stable coating composition comprising an active hydrogen-containing compound and a blocked polyisocyanate of the formula:

$$R\text{-}Y_m$$

wherein R is an m valent aliphatic, cycloaliphatic, heterocyclic or aromatic residue, m is an integer greater than 1 and Y is a blocking group, the improvement whereby said composition is curable by heat unblocking at 100° C. to 120° C., and each Y, which may be the same or different, is

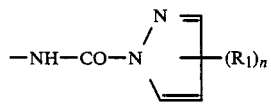

wherein $R_1$ is, or, where n is more than 1, each $R_1$, which may be the same or different, is a $C_1$–$C_4$ alkyl, $C_1$–$C_4$ alkenyl, phenyl $C_1$–$C_4$ alkyl, phenyl, $NO_2$, <halogen or

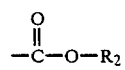

group where $R_2$ is a $C_1$–$C_4$ alkyl group; and n is 0, 1, 2 or 3, provided that, when R is an aromatic residue the groups Y are not directly attached to an aromatic nucleus.

2. A composition according to claim 1 wherein, in said blocked polyisocyanate, at least one Y is

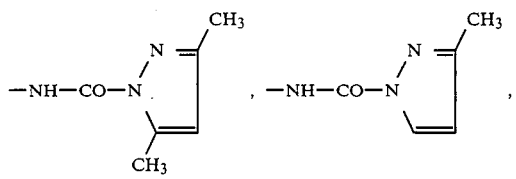

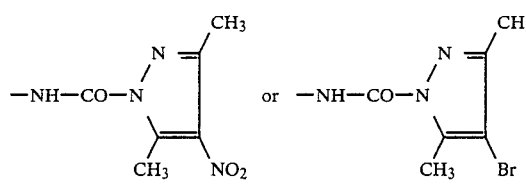

3. A composition according to claim 2 wherein in at least one Y is

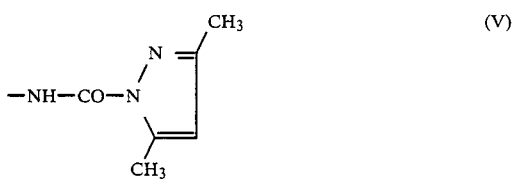 (V)

4. A composition according to claim 1 wherein, in said blocked polyisocyanate, m is from 2 to 6.

5. A composition according to claim 1 wherein, in said blocked polyisocyanate, R is a hydrocarbon group optionally substituted by an alkoxy group.

6. A composition according to claim 1 wherein, in said blocked polyisocyanate, R is a divalent radical derived from isophorone of formula

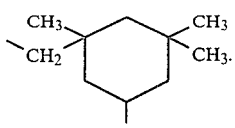

7. A composition according to claim 1 wherein said blocked polyisocyanate has a biuret structure or an allophanate group.

8. A composition according to claim 1 wherein said active hydrogen-containing compound is an amine or an alcohol.

9. A composition according to claim 8 wherein said active hydrogen-containing compound is 1,4-butanediol.

10. A composition according to claim 1 further comprising a catalyst.

11. A composition according to claim 10 wherein said catalyst is dibutyl tin dilaurate or tri-ethylene diamine.

12. A composition according to claim 1 wherein said active hydrogen-containing compound is a pigment carrier containing active hydrogen groups, said composition further comprising a pigment.

13. A composition according to claim 12 having 0.5 to 2 blocked isocyanate groups per active hydrogen-containing group.

14. A composition according to claim 1 wherein, in said polyisocyanate, R is an aliphatic group.

15. A composition according to claim 1 wherein, in said polyisocyanate, R is an cycloaliphatic group.

16. A composition according to claim 1, wherein said polyisocyanate is a di-isocyanate.

* * * * *